United States Patent [19]

Dodd

[11] 4,249,026

[45] Feb. 3, 1981

[54] SEPARATING 2,5-XYLENOL FROM A MIXTURE OF 2,5-XYLENOL AND 2,4-XYLENOL

[75] Inventor: John R. Dodd, Ponca City, Okla.

[73] Assignee: Conoco, Inc., Ponca City, Okla.

[21] Appl. No.: 97,248

[22] Filed: Nov. 26, 1979

[51] Int. Cl.³ .................. C07C 37/68; C07C 37/86
[52] U.S. Cl. ................................ 568/750; 568/788
[58] Field of Search ............... 568/750, 751, 788, 793

[56] References Cited

U.S. PATENT DOCUMENTS

| 2,435,087 | 1/1948 | Luten | 568/750 |
| 2,802,884 | 8/1957 | D'Alelio | 568/788 |
| 2,917,487 | 12/1959 | Jones et al. | 568/750 |
| 3,584,058 | 6/1971 | Hahn | 568/793 |

FOREIGN PATENT DOCUMENTS

| 582057 | 11/1946 | United Kingdom | 568/750 |
| 969415 | 9/1964 | United Kingdom | 568/751 |

OTHER PUBLICATIONS

Kunin "Ion Exchange Resin", TP i56 I 16.

Primary Examiner—Werren B. Lone
Attorney, Agent, or Firm—Cortlan R. Schupbach, Jr.

[57] ABSTRACT

A mixture of 2,4-/2,5-xylenol can be alkylated with a suitable alkylating agent over a strongly acidic divinylbenzene-styrene copolymer to afford a greater amount of 4-t-alkyl-2,5-xylenol than 6-t-alkyl-2,4-xylenol provided the alkylation is carried out at a suitably low temperature of up to 60° C.

3 Claims, No Drawings

SEPARATING 2,5-XYLENOL FROM A MIXTURE OF 2,5-XYLENOL AND 2,4-XYLENOL

This invention relates to the selective alkylation of 2,5-xylenol in the presence of 2,4-xylenol. More specifically, this invention relates to a method for such alkylation by contacting the 2,4-xylenol/2,5-xylenol mixture with a polymer-bound sulfonic acid catalyst at a temperature of about 60° C. or less in the presence of a suitable alkylating agent.

For many applications it is desirable to separate admixtures of 2,4-xylenol and 2,5-xylenol into the individual isomers such that each is available in high purity. These materials cannot be separated by fractional distillation since these isomers boil within 0.1° C. of one another. Consequently other methods of achieving this separation must be utilized. The present invention not only provides a method for selectively alkylating 2,5-xylenol in the presence of 2,4-xylenol but also provides a method for the separation of 2,5-xylenol from 2,4-xylenol in a mixture of these isomers using this selective alkylation followed by a selective dealkylation. The key step in the present invention is the selective alkylation of 2,5-xylenol in a 2,4-/2,5-xylenol mixture achieved by alkylating this mixture in the presence of a polymer-bound sulfonic acid catalyst and a suitable alkylating agent at a temperature of up to 60° C. and preferably up to 40° C.

The art contains many references relating to phenolic alkylations and dealkylations. The use of polymer-bound sulfonic acid catalysts for alkylation and dealkylation is known. U.S. Pat. No. 2,802,884 describes the use of a sulfonic acid catalyst on a resin matrix as an alkylation/dealkylation catalyst at temperatures greater than or equal to 100° C. Selective alkylation, selective dealkylation, or isomer separation, however, is not shown.

U.S. Pat. No. 3,584,058 likewise shows such alkylations. Further alkylations can be seen from the *Journal of Organic Chemistry*, Volume 22, page 988 (1957).

Processes for the separation and purification of 2,5-xylenol and 2,4-xylenol from their admixture are known. Representative but not exhaustive of the prior art is British Pat. No. 582,057 which describes a method for separating 2,4-xylenol and 2,5-xylenol involving the butylation of a 2,4-/2,5-xylenol mixture and then treating the butylated mixture with an aqueous alkali solution to yield an aqueous insoluble organic phase of 6-t-butyl-2,4-xylenol and an aqueous phase of the salt of 4-t-butyl-2,5-xylenol. The aqueous phase is acidified to yield 4-t-butyl-2,5-xylenol. Each of the separated butylated xylenols are debutylated and distilled to afford the purified 2,4-xylenol and 2,5-xylenol. British Pat. No. 706,107 teaches that the use of a sulfuric acid catalyst alkylates only 2,4-xylenol with diisobutylene while 2,5-xylenol is unchanged. A base is then used to extract unchanged 2,5-xylenol. U.S. Pat. No. 2,917,487 shows the separation of 2,4-/2,5-xylenol mixtures by selective resinification. German Patent No. 1,153,027 teaches separation of 2,4-/2,5-xylenol mixtures by butylation using isobutylene catalyzed by perchloric acids and the subsequent separation of the isomeric butylated xylenols by fractional distillation. Desired individual isomers are then debutylated.

In copending application Ser. No. 47,190 filed June 8, 1979, I disclosed a method for the selective dealkylation of 4-tertiary-alkyl-2,5-xylenol from admixture with 6-tertiary-alkyl-2,4-xylenol by contacting the mixture of alkylated xylenols with a polymer-bound sulfonic acid catalyst at temperatures of up to 60° C. and pressures of from about 0.5 to 5 atmospheres. The critical step of that invention is the use of a sufficiently low temperature to provide selective dealkylation. The present invention, involving critical temperatures for selective alkylation of a 2,4-/2,5-xylenol admixture allows an even greater use of my previous invention since the starting alkylated mixture obtained upon application of the present invention is highly favorable for use in that earlier described process.

The process of the present invention is very similar to that previously described except for the presence of an alkylating agent. The alkylation/dealkylation reaction can be carried out under similar conditions. The absence or presence of an alkylating agent determines whether the xylenols predominantly alkylate (agent present) or dealkylate (agent absent) during a reaction carried out under these same conditions.

None of the teachings of the prior art indicate a temperature effect to be critical in such alkylations of 2,4-/2,5-xylenol mixtures. The present invention provides a method for selectively alkylating a 2,4-/2,5-xylenol mixture to afford a greater amount of 4-t-alkyl-2,5-xylenol than 6-t-alkyl-2,4-xylenol comprising (a) contacting a 2,4-/2,5-xylenol mixture with an alkylating agent in the presence of a strongly acidic sulfonated divinylbenzene-styrene copolymer at a temperature of up to 55° C. and then fractionating the resulting reaction mixture to remove all unreacted xylenols. Removal of the unreacted xylenols yields a mixture containing predominantly 4-t-alkyl-2,5-xylenol and 6-t-alkyl-2,4-xylenol. This mixture can then be selectively dealkylated using the process described in my copending application Ser. No. 47,190 filed June 8, 1979, hereby incorporated by reference in its entirety into the present application. The selective dealkylation of 4-t-alkyl-2,5-xylenol while an admixture with 6-t-alkyl-2,4-xylenol is achieved by contacting a mixture of these materials with a strongly acidic polymer-bound sulfonic acid catalyst at temperatures up to or equal to 60° C. and pressures of from about 0.5 to about 5 atmospheres.

Thus the present invention provides a method for the selective alkylation of 2,5-xylenol while in the presence of 2,4-xylenol (i.e. yields a greater amount of 4-t-alkyl-2,5-xylenol as compared to 6-t-alkyl-2,4-xylenol) by contacting the 2,4-/2,5-xylenol mixture with an alkylating agent which will yield a tertiary-alkyl group in the presence of a strongly acidic sulfonated divinylbenzene-styrene copolymer at a temperature of up to 55° C. Application of the process yields upon removal of the unreacted xylenols a large amount of 4-t-alkyl-2,5-xylenol which can then be selectively dealkylated in the presence of a highly acidic sulfonated divinylbenzene-styrene copolymer at a temperature of up to 60° C.

The alkylating agents useful in the instant invention are generally those which afford a tertiary-alkyl group. Representative examples of such alkylating agents are isobutylene, 2-methyl-1-butene, 2-methyl-1-pentene, and 2-methyl-1-heptene. These materials are likewise preferred. Isobutylene is most preferred and is used throughout in the specifications to illustrate the instant invention.

The instant invention is carried out at a temperature of 60° C. or less and preferably at a temperature of 40° C. or less for maximum selectivity. The instant invention is thus highly preferred for processes where 2,5-xylenol purification is of primary concern. The instant invention yields an alkylated 2,4-/2,5-xylenol mixture which is richer in 4-t-alkyl-2,5-xylenol than 6-t-alkyl-2,4-xylenol. Such a mixture is preferred for subsequent selective debutylation steps in 2,5-xylenol separation and purification as described in my copending application Ser. No. 47,190 filed June 8, 1979. Direct alkylation of a 2,4-/2,5-xylenol mixture using conventional homogenous acidic catalysts, such as sulfuric acid, in contrast produces a greater amount of 6-t-alkyl-2,4-xylenol than 4-t-alkyl-2,5-xylenol in the t-alkylated product mixture. The present invention is dependent upon a critical temperature limitation.

The instant invention is more concretely described with reference to the examples below wherein all parts and percentages are by weight unless otherwise specified. The examples are provided to illustrate the instant invention and not to limit it.

EXAMPLE 1

A cresylic acid mixture containing 2,4-xylenol and 2,5-xylenol in addition to other components was used as the cresylic component in this example. This mixture consisted of 19.05% 2,3-xylenol, 34.6% 2,4-/2,5-xylenols (composition=48.75% 2,5-xylenol and 51.25% 2,4-xylenol), 9.88% 2,6-xylenol, 29.31% 2,4,6-trimethylphenol, 3.53% 2,3,6-trimethylphenol, 2.89% pentamethylbenzene, and small amounts of phenol and cresols.

A solution of 748 grams of the above cresylic acid mixture and 254 grams (4.54 moles) of isobutylene was passed through a stainless steel continuous tubular reactor having a catalyst bed volume of 66.4 ml. The reactor was packed with 44 g of dry Amberlyst-15 ® catalyst (trademark of and sold by Rohm and Haas Company), a highly acidic sulfonated styrene-divinylbenzene copolymer catalyst. During the reaction period, the reactor was maintained at a specific test temperature and a 3 pounds per square inch gauge (psig) backpressure. The feed mixture was pumped into the reactor at a rate of 0.94 ml per minute, corresponding to a liquid hourly space velocity (LHSV) of 0.85.

The reaction was begun and the first 93 grams of the product stream was discarded to allow the continuous reaction to come to equilibrium. The remaining 853 grams of the reaction run were collected and analyzed using gas chromatography. The following composition was obtained.

Isobutylene: 0.10%
Tertiary Butanol: 0.38%
Isobutylene Oligomers: 9.52%
2,6-Xylenol: 0.76%
2,4-/2,5-Xylenols: 10.13%
2,3-Xylenol: 2.65%
2,4,6-Trimethylphenol: 22.78%
2,3,6-Trimethylphenol: 0.87%
Pentamethylbenzene: 1.35%
6-t-Butyl-2,4-xylenol: 7.77%
4-t-Butyl-2,6-xylenol: 7.20%
6-t-Butyl-2,3-xylenol: 11.46%
4-t-Butyl-2,5-xylenol: 12.04%
1-t-Butoxy-4-t-butyl-2,5-xylene: 0.17%
4-t-Butyl-2,3,6-trimethylphenol: 1.33%
4-6-Di-t-butyl-2,3-xylenol: 8.55%
Unidentified components: 0.3%

In this first experiment, 62.5% of the 2,4-/2,5-xylenol was butylated.

EXAMPLES 2 THROUGH 20

Experiments 2 through 20 were carried out in a similar manner with the results shown in Table 1.

In this table, the column headed R.T. shows the residence time in the reactor in hours. The column headed M shows the moles of isobutylene divided by the moles of xylenol in the feed mixture. The column headed Conv (IB) is the percent conversion of isobutylene. Conv (24/25) is the percent conversion of 2,4-/2,5-xylenols, Conv (26) is the percent conversion of 2,6-xylenol, Conv (23) is the percent conversion of 2,3-xylenol. The column headed R is the ratio of 4-t-butyl-2,5-xylenol to 6-t-butyl-2,4-xylenol in the product stream.

TABLE 1

|    | T (°C.) | P (psig) | R.T. (Hrs.) | M    | Conv (IB) | Conv (24/25) | Conv (26) | Conv (23) | R    |
|----|---------|----------|-------------|------|-----------|--------------|-----------|-----------|------|
| 1  | 38      | 3        | 1.18        | 1.16 | 99.6      | 62           | 90        | 82        | 1.55 |
| 2  | 71      | 3        | 1.13        | 0.93 | 99.7      | 46           | 91        | 72        | 0.11 |
| 3  | 50      | 3        | 1.41        | 0.93 | 99.5      | 53           | 70        | 80        | 1.08 |
| 4  | 90      | 3        | 1.47        | 0.93 | 99.6      | 37           | 99        | 53        | 0.06 |
| 5  | 111     | 3        | 2.42        | 0.93 | 97.7      | 23           | 100       | 62        | 0.06 |
| 6  | 90      | 3        | 0.91        | 1.16 | 99.4      | 43           | 98        | 63        | 0.11 |
| 7  | 37      | 3        | 0.94        | 1.16 | 96.5      | 57           | 62        | 82        | 1.57 |
| 8  | 61      | 3        | 1.40        | 0.93 | 99.9      | 44           | 94        | 75        | 0.18 |
| 9  | 75      | 3        | 1.09        | 0.93 | 99.8      | 42           | 96        | 64        | 0.07 |
| 10 | 65      | 3        | 1.04        | 0.99 | 99.8      | 54           | 93        | 81        | 0.29 |
| 11 | 71      | 3        | 1.23        | 0.99 | 99.8      | 48           | 93        | 74        | 0.16 |
| 12 | 70      | 3        | 2.48        | 0.99 | 99.8      | 48           | 98        | 72        | 0.09 |
| 13 | 75      | 3        | 1.03        | 0.99 | 99.8      | 47           | 91        | 76        | 0.17 |
| 14 | 81      | 3        | 1.10        | 0.99 | 99.7      | 46.5         | 93        | 72        | 0.07 |
| 15 | 70      | 3        | 1.23        | 1.50 | 99.5      | 70           | 96        | 87        | 0.66 |
| 16 | 80      | 3        | 1.29        | 1.50 | 99.7      | 57           | 98        | 80        | 0.21 |
| 17 | 90      | 3        | 1.25        | 1.50 | 99.6      | 50           | 100       | 71        | 0.09 |
| 18 | 85      | 3        | 1.25        | 1.50 | 99.6      | 57           | 100       | 77        | 0.15 |
| 19 | 85      | 50       | 1.23        | 1.50 | 99.8      | 51           | 100       | 71        | 0.08 |
| 20 | 85      | 3        | 1.69        | 1.50 | 99.7      | 57           | 100       | 75        | 0.13 |

EXAMPLES 21 THROUGH 30

The cresylic acid mixture whose composition was given in Example 1 was used. A feed consisting of 950 grams of this material and 440 grams of isobutylene was pumped into a 300 ml autoclave set up for continuous operation. The autoclave was equipped with a back-pressure regulator, condenser, and liquid sample collector. Samples were collected periodically during operation and analyzed by gas chromatrography. Other runs at varying temperatures were repeated at these different temperatures. The results are set forth in Table 2 wherein the column headings are the same as those described in Table 1.

TABLE 2

| | T (°C.) | P (psig) | R.T. (hrs) | M | Conv (IB) | Conv (24/25) | Conv (26) | Conv (23) | R |
|---|---|---|---|---|---|---|---|---|---|
| 21 | 77 | 3 | 1.71 | 1.33 | 93 | 65 | 77 | 84 | 0.77 |
| 22 | 77 | 2 | 2.77 | 1.34 | 96 | 69 | 81 | 86 | 0.71 |
| 23 | 91 | 2 | 2.90 | 1.34 | 97 | 62 | 90 | 86 | 0.40 |
| 24 | 90 | 2 | 2.22 | 1.56 | 95 | 68 | 91 | 85 | 0.55 |
| 25 | 91 | 2 | 4.44 | 1.56 | 98 | 63 | 96 | 85 | 0.31 |
| 26 | 93 | 3 | 1.82 | 1.73 | 93 | 70 | 90 | 87 | 0.59 |
| 27 | 72 | 3 | 1.50 | 1.73 | 92 | 76 | 85 | 86 | 0.92 |
| 28 | 53 | 3 | 3.42 | 1.73 | 96 | 86 | 87 | 89 | 1.08 |
| 29 | 72 | 3 | 1.03 | 0.93 | 96 | 56 | 71 | 77 | 0.83 |
| 30 | 90 | 3 | 1.01 | 0.93 | 98 | 62 | 85 | 80 | 0.40 |

EXAMPLE 31

A sulfuric acid-catalyzed butylation was carried out using a cresylic acid mixture consisting of 89.43% 2,4-/2,5-xylenols in a 50/50 ratio, 7.40% 2,3-xylenol, 1.25% pentamethylbenzene, and 1.92% of minor unidentified components. A 200 gram sample of the cresylic acid mixture and 3 grams of concentrated sulfuric acid were placed in a 500 ml 3-necked flask equipped with a magnetic stirrer, condenser, thermomometer and gas inlet tube. Isobutylene was bubbled into the stirred solution which was maintained at 35° C. by adjusting the rate of isobutylene flow and using a combination of external heating and cooling as needed. Small samples were periodically removed for gas chromatographic analysis. The introduction of isobutylene was stopped after several hours when the reaction mixture weighed a total of 334 grams.

The reaction mixture was poured into a separatory funnel containing 200 ml of water. The pH of the aqueous phase was adjusted to 10 by adding dilute caustic. The basic aqueous phase was removed and the reaction mixture was washed with saturated sodium chloride solution. The organic phase was taken up in 200 ml of ether added to break an emulsion. The resulting ether was washed with several 200 ml portions of water and saturated sodium chloride solution. This solution was then dried over anhydrous sodium sulfate and the major portion of the ether was removed. The crude product was analyzed by gas chromatography. The gas chromatographic analysis indicated the following composition.

Ether: 3.71%
Isobutylene Oligomers: 12.4%
1-t-Butoxy-4-t-butyl-2,5-xylene: 18.28%
6-t-Butyl-2,4-xylenol: 42.58%
2,4-/2,5-xylenols: 6.58%
4-t-Butyl-2,5-xylenol: 10.93%
Unidentified Components: 5.5%

The relative amounts of butylated and unbutylated 2,4-/2,5-xylenols obtained by application of the instant invention at 38° C. (Example 1) and from alkylation at 35° C. using sulfuric acid (Example 3) are set forth in Table 3. In Table 3, 2,4-/2,5 indicates 2,4-/2,5-xylenol, 24M6B indicates 6-t-butyl-2,4-xylenol, 25M4B indicates 4-t-butyl-2,5-xylenol, and Cmpd. A indicates 1-t-butoxy-4-t-butyl-2,5-xylene. The table shows relative amounts based on 25M4B with a value of 10.0. The values in parenthesis indicate relative amounts based on 100 parts of these four substances by weight.

TABLE 3

| Component | Polymer-Bound Sulfonic Acid Run Example 1 | Sulfuric Acid Run Example 3 |
|---|---|---|
| 24/25 | 8.4 (33.6) | 6.1 (8.4) |
| 24M6B | 6.5 (25.8) | 39.1 (54.3) |
| 25M4B | 10.0 (40.0) | 10.0 (13.9) |
| Cmpd. A | 0.1 (0.6) | 16.5 (23.3) |

It is readily apparent that by using the method of the present invention a mixture of t-alkylated 2,4-/2,5-xylenols heavily enriched in 4-t-alkyl-2,5-xylenol can be obtained; this method consists of alkylating a 2,4-/2,5-xylenol mixture over a strongly acidic sulfonated divinylbenzene-styrene copolymer under low temperature conditions. The resulting t-alkylated mixture after xylenol removal is then useful as a feed for selective dealkylation over the same catalyst at temperatures of up to 60° C. in an improved method of separating 2,4-/2,5-xylenol mixtures.

While certain embodiments and details have been shown for the purpose of illustrating this invention, it will be apparent to those skilled in this art that various changes and modifications may be made herein without departing from the spirit or scope of the invention.

I claim:

1. A method for separating 2,5-xylenol from 2,4-xylenol/2,5-xylenol mixtures comprising
    (a) preferentially alkylating 2,5-xylenol in said mixture in the presence of an alkylating agent selected from the group consisting of isobutylene, 2-methyl-1-propene, 2-methyl-1-butene, 2-methyl-1-pentene and 2-methyl-1-heptene and a strongly acidic sulfonated divinylbenzene-styrene copolymer at a temperature of up to 60° C. to yield predominantly 4-t-alkyl-2,5-xylenol,
    (b) fractionating the resulting reaction mixture to remove all unreacted xylenols,
    (c) selectively dealkylating 4-t-alkyl-2,5-xylenol while in admixture with 6-t-alkyl-2,4-xylenol to yield a mixture containing predominantly 2,5-xylenol and 6-t-alkyl-2,4-xylenol by heating the mixture to a temperature of up to 60° C. at a pressure of from about 0.5 to about 5 atmospheres in the presence of a polymer bound sulfonic acid catalyst, then fractionating the resulting mixture to separate 2,5-xylenol from the remaining components in the mixture obtained upon selective dealkylation.

2. A method as described in claim 1 wherein isobutylene is the alkylating agent.

3. A method as described in claim 2 wherein the the butylation reaction is carried out at a temperature up to 40° C.

* * * * *